(12) United States Patent
Dennis et al.

(10) Patent No.: US 7,195,780 B2
(45) Date of Patent: Mar. 27, 2007

(54) NANOPARTICLE DELIVERY SYSTEM

(75) Inventors: Donn M. Dennis, Gainesville, FL (US); Charles R. Martin, Gainesville, FL (US); Richard J. Rogers, Gainesville, FL (US); Jon D. Stewart, Gainesville, FL (US)

(73) Assignee: University of Florida, Gainesville, FL (US)

(*) Notice: Subject to any disclaimer, the term of this patent is extended or adjusted under 35 U.S.C. 154(b) by 507 days.

(21) Appl. No.: 10/274,829

(22) Filed: Oct. 21, 2002

(65) Prior Publication Data

US 2004/0076681 A1   Apr. 22, 2004

(51) Int. Cl.
 A61K 9/14   (2006.01)
 A61K 9/50   (2006.01)
 B32B 5/16   (2006.01)
(52) U.S. Cl. .................. 424/502; 424/489; 424/501; 428/402.2; 428/402.22
(58) Field of Classification Search ................ 424/489, 424/501, 502
 See application file for complete search history.

(56) References Cited

OTHER PUBLICATIONS

Lvov Y.M and Price R.R., "Nanoparticle/ polyion on microtemplates (lipid tubules and latex spheres)" Colloids and Surfaces B: Biointerfaces, (2002) 23/4 pp. 251-256.
Lvov, Yuri M. et al., "Imaging Nanoscale Patterns on Biologically Derived Microstructures" Langmuir (2000), 16(14), pp. 5932-5935.
Demoustier-Champagne S. and Legras R., "Electrosynthesis of Polypyrrole Nanotubes Using Particle Track-etched Membranes as Template" Journal de Chimie Physique et de Physico-Chimie Biologique, (1998) 95/6 pp. 1200-1203.
Malet J. et al., "Deposition of nanosized particles in cylindrical tubes under laminar and turbulent flow conditions" Journal of Aerosol Science, (2003) 31/3 pp. 335-348.
Burkett, Sandra L. and Mann, Stephen, "Spatial organization and patterning of gold nanoparticles on self-assembled biolipid tubular templates" Chem. Commun. (Cambridge) (1996), (3), pp. 321-322.
Majeti N.V. Ravi Kumar, "Nano and Microparticles as Controlled Drug Delivery Devices", J. Pharm. Pharmaceut Sci 3(2): 234-258 (2000).
Kshama B. Jirage et al., "Nanotubule-Based Molecular-Filtration Membranes", Science, vol. 278, pp. 655-658 (1997).
Matsuhiko Nishizawa et al., "Metal Nanotubule Membranes with Electrochemically Switchable Ion-Transport Selectivity", Science, vol. 268, pp. 700-702 (1995).
D. H. Pearson and R. J. Tonucci, "Nanochannel Glas Replica Membranes", Science, vol. 270, pp. 68-70 (1995).
Charles R. Martin, "Nanomaterials: A Membrane-Based Synthetic Approach", Science, vol. 266, pp. 1961-1966 (1994).
Crispin R. Dass and Tao Su, "Particle-Mediated Intravascular Delivery of Oligonucleotides to Tumors: Associated Biology and Lessons from Genotherapy", Drug Delivery, 8: 191-213 (2001).
Gabor M. Rubanyi, "The Future of Human Gene Therapy", Molecular Aspects of Medicine, 22, pp. 113-142 (2001).
Feng Liu and Leaf Huang, "Development of Non-viral Vectors for Systemic Gene Delivery", journal of Controlled Release, 78, pp. 259-266 (2002).
Gary Hsich et al., "Critical Issues in Gene Therapy for Neurologic Disease", Human Gene Therapy, 13: pp. 579-604 (2002).
Kathryn Senior, "Nano-dumping' with Drug Delivery Potential", Molecular Medicine Today, p. 321 (Aug. 2998).

*Primary Examiner*—Carlos A. Azpuru
(74) *Attorney, Agent, or Firm*—Brinks Hofer Gilson & Lione

(57) ABSTRACT

The invention relates to the nanotubes of various sizes and composed of a wide variety of materials, or combination of materials. The invention also describes the use of such nanotubes for the delivery of various payloads and, in particular, for the in vivo delivery of bioactive substances.

33 Claims, 4 Drawing Sheets (A)

Scheme 1. End-Functionalized Polylactides:

(B)

Scheme 2

NANOPARTICLE DELIVERY SYSTEM

STATEMENT OF GOVERNMENTAL INTEREST

The subject matter of this application has been supported by a research grant from the National Science Foundation (Grant Number NSF: EEC 02-10580). The government may have certain rights in this invention.

BACKGROUND

Currently, there is enormous interest in using nanotechnology for a variety of applications, including biomedical ones. Nanoparticles offer many advantages when used for applications such as the delivery of bioactive agents (e.g., DNA, AIDS drugs, immunosuppressants, chemotherapeutics), and drug uptake and degradation (e.g., enzyme encapsulation). In addition, nanotechnology offers considerable potential when applied in other areas, such as agricultural processes (e.g., plant genetics; or controlled fertilizer and pesticide release using sensor technology linked to the payload release mechanism), industrial synthetic processes, and environmental applications (e.g. ultra-effective decontamination and disinfection of areas contaminated with toxic chemicals and/or biotoxins such as bacteria or viruses).

In the biomedical area there are currently a number of viral vector systems under development for gene delivery. Common viral vectors being studied include the adenovirus, adeno-associated virus, retrovirus and herpes simplex virus. However, such systems have a number of disadvantages.

Adenoviruses are non-enveloped particles of size 70 nm containing a linear double stranded DNA of approximately 36,000 base pairs. They are easily prepared with high titers and can infect a wide range of cells, including non-dividing cells. However, adenoviruses cause mild illness in humans and can elicit a strong host immune response. Although recently developed modified adenovirus vectors exhibit a significantly reduced immune response, the viral replication and expression of such vectors are limited.

Adeno-associated viruses have a particle diameter of 20 nm. This small particle size limits the size of the DNA molecule the virus can carry. In addition, adeno-associated viruses are not easily prepared. Particular problems are low production yields and contamination associated with helper virus.

Retroviruses are spherical, enveloped particles 80–100 nm in diameter. Retroviruses have been widely used as vectors for DNA delivery. However, they can only be used to target actively dividing cells. In addition, retroviruses do not accommodate large DNA inserts readily. Major problems also occur in the production of replication competent retrovirus. Such problems typically result in low titers. In addition, biosafety is the major concern for the production of HIV-based vectors.

Herpes simplex viruses are particles of 100 nm diameter containing enveloped, double-stranded DNA virus of approximately 150,000 base pairs. These viruses have a large loading capacity for foreign genes and are able to infect a wide range of cells. In addition, the virus genome remains episomal after infection, thus eliminating the possibility of opportunistic malignant insertional mutagenesis of the host genome. Herpes viruses have been exploited for specific gene transfer trials into the central nervous system. However, herpes viruses can be toxic and inflammatory, although recent advances have decreased their cytotoxicity.

In spite of the availability of replication defective viruses, concerns about the safety and efficiency of such viral vectors has generated interest in the development of nonviral gene transfer systems such as naked DNA, liposome-DNA complexes, and cell-based delivery systems.

In addition, particle-based delivery systems have been investigated for the delivery of oligonucleotides and other bioactive agents. For example, particle-based intravascular delivery of oligonucleotides has been proposed for the selective targeting of tumor vascular endothelial cells (Chispin R. Dass, "Particle-Mediated Intravascular Delivery of Oligonucleotides to Tumors: Associated Biology and Lessons from Genotherapy" Drug Delivery, 8: 191–213 (2001)). Microspheres have been proposed as providing the site-specific distribution of drugs to, and minimization of loss from, the target site. By selecting appropriately sized particles, such particles become trapped in the vasculature of selected tissues where they release their drug load in a controlled and sustained manner.

Important factors related to the use of particle-based delivery systems include the particle structure and size; surface properties; biocompatibility including immunogenic properties and the ability to avoid detection by the reticuloendothelial system of the body for variable lengths of time ("stealthiness"); toxicity; biodegradability; and the mechanism and timing of release of the payload from the particle. Other factors, such as the cost of particle formulation and payload loading, the ease of manufacture, and the ability to recover unloaded payload are also important.

Hence, despite the availability of the above systems, there is a continuing need for a new system for the delivery of bioactive agents and other payloads.

SUMMARY

In one aspect, the present invention provides a nanotube comprising: a hollow tubular body comprising a first end and a second end, wherein the first end is open; and a first end cap positioned over the first open end, wherein the end cap is attached to the hollow tubular body by a covalent bond and the particle has a maximum dimension of less than 100 μm. Alternatively, the nanocap can be held in place by electrostatic forces, hydrogen bonding or other non-covalent interactions.

In one embodiment the second end is open and a second end cap is positioned over the second open end, wherein the second end cap is attached to the hollow tubular body by a covalent bond.

In another aspect, the present invention provides a method for the in-vivo delivery of a bioactive agent comprising: administering the bioactive agent contained within a nanotube, wherein the nanotube comprises a hollow tubular body defining an inner void and having at least one open end and a first end cap positioned over the open end, wherein the end cap is attached to the hollow tubular body by a covalent bond or other type of force as previously described and the hollow tubular body has a maximum dimension of less than 100 μm.

In yet another aspect, the present invention is directed to a nanotube delivery system comprising a hollow tubular body defining an inner void, comprising a first open end and a second open end and a payload material linked to a surface of the hollow tubular body.

DETAILED DESCRIPTION

Nanotubes

Figure 1:
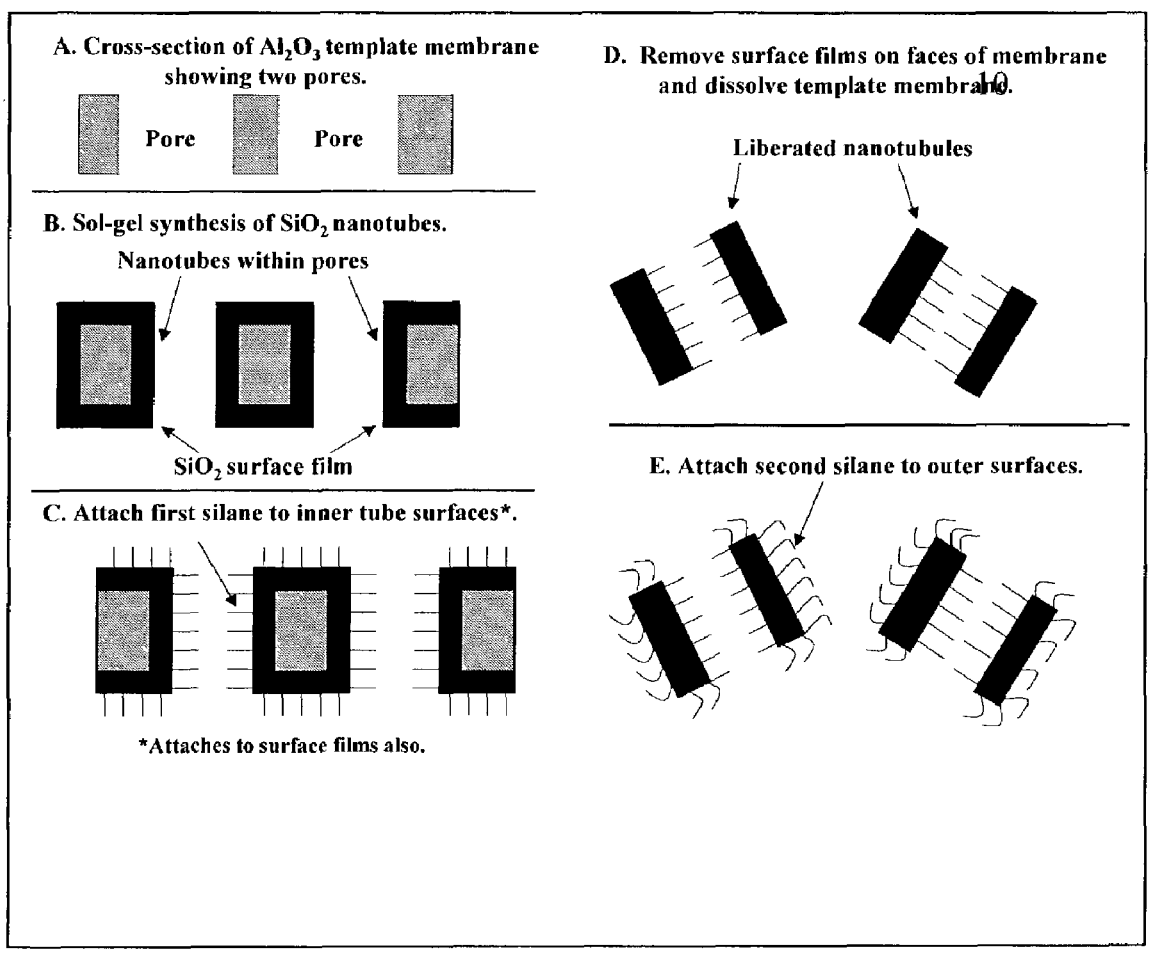
FIGS. 1(A)–(E) are schematic diagrams showing the procedure used to attach different silanes to the inner and outer surfaces of the nanotubes.

Particle-based delivery systems offer the potential for payload delivery and release. In the biomedical area, such delivery systems provide a mechanism for the targeted delivery and release of DNA and other bioactive agents to selected sites within the body. The present invention discloses nanoparticles in the form of tubular bodies ("nanotubes"). Nanotubes can be produced in a wide range of sizes and composed of a wide range of materials, or combination of materials. Nanotubes can be either hollow or solid and can be prepared having a highly monodisperse size distribution.

In one embodiment of the present invention the nanotube is hollow and both ends of the nanotube are open. In another embodiment, one or both ends of the nanotube are closed.

Capped-Nanotubes

In yet another embodiment of the present invention, an open nanotube end can be blocked with an end-cap ("nanocap") so as to prevent the release of a payload material present within the void formed by the nanotube. A "capped nanotube" is a nanotube having a nanocap attached to at least one end of the nanotube. Suitable "nanocaps" include, for example, nanoparticles having a diameter slightly larger than the inside diameter of the nanotube, so as to occlude the open end of the nanotube.

The term "nanoparticle" refers to a piece of matter. In a preferred embodiment, the nanoparticle is of a spherical or spheroidal form. However, nanoparticles of other shapes, including ellipsoidal, cylindrical, and irregular can also be used as nanocaps. Nanocaps can be composed of materials that are chemically or physically similar (or dissimilar) to the nanotube.

Payload Materials

A nanotube has unique attributes which make it an ideal candidate for many biomedical, agricultural, veterinary, environmental, and industrial applications requiring the delivery of materials. Nanotubes of the present invention provide a means of delivering many "payload" materials to a required site. If necessary, nanotubes also provide a means of releasing the payload after delivery. Potential payload materials include bioactive compounds, industrial chemicals, fertilizers, pesticides, environmental decontaminatants and many other chemicals. "Delivery" includes the transfer of the payload to a specific site or sites within a system.

The mechanism used to deliver the nanoparticles depends on the specific application. For example, a bioactive compound can be delivered to a required part or parts of a human or animal body via an intravenous, intradermal, subcutaneous, oral (e.g., inhalation), transdermal (i.e., topical), or transmucosal route. Fertilizers or pesticides can be incorporated into nanotubes and delivered by methods well known in the art such as aerial spraying or mechanical application. Nanotubes have an application in situations where a payload must be delivered to a specific site and/or when the release of the payload must be controlled.

In one embodiment of the present invention a payload is attached to an inside or outside surface of a hollow nanotube having at least one open end. For example, the payload material can be attached to a inner or outer surface of such an open-ended nanotube by a covalent or other chemical bond. If the payload material is to released upon delivery, the payload can be attached by a chemically labile bond, such as an ester linkage. The release of the payload material occurs upon hydrolization of the bond. Alternatively, the nanotube is prepared from a degradable material. Here, the payload is released as the nanoparticle degrades.

In another embodiment, the payload is encased within a hollow nanotube having closed ends. Such nanotubes provide significant advantages over nanospheres because payloads can be more easily and inexpensively loaded into the payload space using various existing technologies (e.g., electrophoresis or filtration). The nanotube is then sealed to capture the payload material.

The sealed nanotube can be prepared from a material which degrades over time and/or when subjected to a particular environment. This will result in the release of the payload as the nanotube degrades. For example, the nanotube prepared for in-vivo application can be prepared from a biodegradable material. A nanotube prepared to deliver fertilizer or pesticide can be prepared from a material that degrades over time when subjected to defined environmental conditions.

Alternatively, the nanotube can be prepared from a material or materials having limited permeability. This allows for the release of the payload over a controlled time period. The nanotube can also be prepared using materials that swell after a fixed time, resulting in increased diffusion of the nanotube payload.

In yet another embodiment of the present invention, the payload material is incorporated into the material making up the nanotube. For example, the payload material may be incorporated into a degradable nanotube. In this embodiment, the nanotube can be solid, having no inner void. Solid nanotubes can be prepared by the methods described here.

The present invention also includes a method for delivering and releasing a payload contained in a capped nanotube. This is achieved using nanocaps that are bound to the nanotube in one environment but are released in a different environment. A disulfide link between the nanotube and its nanocap can be used for such applications. In an oxidizing environment, the nanocap remains attached. However, in a reducing environment (such as the interior of a living mammalian cell), the disulfide linkages are broken, making the payload available for delivery.

Other capping methods are also included in the present invention. For example, nanocaps can be held on by electrostatic attractions between the nanocap and the nanotube and released upon a change in the ionic strength of the medium surrounding the nanotube. Alternatively, the nanocap can be held on by acidic and/or basic sites on the nanotube and nanocap. In this case, the nanocap is released by a change in the pH of the medium surrounding the nanotube. The nanocap can also be attached to the nanotube by hydrogen bonding.

Functionalized Nanotubes

In another embodiment, one or more surfaces of the nanotube are functionalized to allow attachment of molecules to the surface. "Functionalized" nanotubes are nanotubes having at least one surface modified to allow for the directed delivery and/or controlled release of the nanotube payload. Nanotubes have distinct inner and outer surfaces, and their open geometry makes accessing and functionalizing these surfaces easy. Different chemical and/or biochemical functional groups can be applied to the inside and outside surfaces of the nanotube. Alternatively, one chemical/biochemical species can be applied to the inside surfaces of the nanotube, a second species to the outside surfaces and a third different species to the nanotube mouths.

For example, directed delivery of the nanotube can be achieved by attaching antibodies or other high affinity ligands to a surface of the nanotube. Such molecules can be linked by covalent or non-covalent bonds.

Controlled release of the payload can be achieved by functionalizing the nanotube mouth regions to a to allow for the attachment of a nanocap via a chemically labile bond. Alternatively, the payload may be attached to a functionalized surface of the nanotube. Such attachment can be via a chemically labile bond, allowing for the release of the payload under specific conditions.

The functionalization of the nanotube surface allows multiple molecular recognition units, such as antibodies directed against different cellular targets or antigens, to be added to the nanotube. Such nanotubes have wide utility in various in-vivo applications. Using drug delivery to the brain as an illustrative example, one molecular recognition unit is used to initially "defeat" the blood brain barrier and allow the nanotube pass through the endothelial cell layer. A second type of molecular recognition unit is used to target the specific brain cell type with drug located in the nanotube payload space. A third type of molecular recognition unit is used for subcellular localization (e.g., delivering payload to nucleus).

In contrast to nanotubes, current biological drug delivery systems, such as the viral vectors being developed for delivery of genetic material (e.g., gene therapy), are much less specific and may indiscriminately infect many types of cells.

Nanotube Payload Delivery

The nanocap can be used to impart several novel functions and degrees of intelligence to the nanotube-nanocap delivery system. These include the sealing of the payload contents within the nanotube in a cost-effective manner.

The nanocap can also provide a mechanism whereby the nanotube payload contents can be selectively released. For example, when used for the in-vivo delivery of a bioactive agent, the nanotube can be designed to release its payload either at the surface of the target cell or within its cytoplasm. This may be achieved by sensing a chemical, physical or biological signal present in the local environment. Alternatively; a remote external energy source, such as ultrasonic irradiation, can be used to selectively release the payload from the nanotube. Time-controlled degradation of the biomaterials used to construct the nanotube and/or nanocaps can also provide a release mechanism.

Depending upon the application, various types of sensors, for example, aptamers, antibodies/proteins, peptides, or high affinity ligands, can be linked to the uncapping/discharge mechanism of the nanocap-nanotube assemble. Thus, the uncapping mechanism can be linked to detection by the sensors on the nanocap-nanotube structure of surface markers on cells types (e.g., cancer cells), proteins in the blood (e.g., PSA for prostate cancer) or drugs in the body (e.g., illicit drugs or therapeutic drugs). These may or may not require the use of energy-bearing biomolecular motors such as, but not limited to, the actin-based system (Dickinson R. B. and Purich D. L., Biophys. J. 2002 82:605–617).

In another embodiment, the nanocap is attached by electrostatic attraction between the nanocap and the nanotube. The cap is released in response to a change in the ionic strength of the medium surrounding the nanotube. Alternatively, the cap can be held on by hydrogen bonding or by acid and/or basic sites on the nanocap/nanotube. The cap is released by a change in the pH or the surrounding medium. The cap may also be held on by covalent bonds that can be cleaved by a specific enzyme, for example, a hydrolase enzyme.

The sensors can be designed to initiate release of payload contents upon detecting stimuli. Such stimuli can include physical stimuli, for example, the temperature, pressure, velocity or acceleration of the nanoparticle; biological stimuli, for example, the presence of normal or abnormal cell types, cellular surface antigens, proteins, oligonucleotides, or toxins; or chemical stimuli, for example, pH, ionic strength, hydration state, redox state, or the presence of therapeutic agents, or toxic drugs such as nerve agents.

For example, one can achieve safe and effective intracellular bioactive agent delivery by attaching the nanocap to the nanotube with covalent bonds (e.g., S—H bonds) that are broken when a specific chemical signal (e.g., high reducing atmosphere of the cytoplasmic environment of the interior of a mammalian cell) is encountered. The ability to incorporate different types of sensor mechanisms for removal of the cap is an extremely powerful approach to the delivery and release (or uptake) of payload contents in an event- and site-specific manner. Specifically, by linking the uncapping mechanism to various sensing modes, the nanotube based drug transport systems can be used to diagnose, treat, and monitor health status. For example, smart nanotubes can detect the appearance of cancer antigens on the walls of cancer cells, cause uncapping which in turn releases an indicator, which in turn makes the urine a distinct color or releases a nontoxic marker which can be readily detected in the breath, and thereby notifies the patient or his/her physician that a cancer cell(s) was encountered in his/her body.

The nanocap can also be used to direct movement of the nanotube-nanocap system. For example, this may be achieved by magnetic guidance of a nanocap containing a magnetically responsive tag.

The nanocap can also contain an energy (e.g., ultrasound) sensitive inert gas that could be used to trigger release of the payload contents from the nanocap-nanotube structure.

Non-Directed Nanotube Delivery Systems

Aside from directing bioactive agent delivery to specific cellular targets via surface functionalization technology, nanotube systems manufactured without surface functionalization still represent a tremendously flexible bioactive agent delivery and release platform. These non-directed systems can be used to easily and economically resolve many of the difficult issues that pharmaceutical companies face during the course of drug development. Nanotube systems provide efficient and cost effective ways to package bioactive agents; to reduce or eliminate solubility problems for lipophilic and/or solid pharmaceutics; to reduce elimination of bioactive agents during passage through the liver, and to provide timed drug release for bioactive agents.

Agricultural, Industrial and Environmental Applications.

Nanotube technology is also applicable to many important industrial and environmental decontamination applications (e.g., compound delivery and release in industrial synthetic reactions, catalysis of industrial chemicals such as insecticides or nerve agents, effective decontamination and disinfection of various biotoxins including viruses and bacteria).

In addition, this technology can be readily applied to agricultural (e.g., plant genetics; or "smart" fertilizer and pesticide release using sensor technology linked to the uncapping mechanism).

Membrane Templates

Nanotubes of the present invention can be synthesized using a template synthesis method. The nanotube synthesis occurs within the pores of a microporous membrane or other solid, as described in Charles R. Martin "Nanomaterials: A Membrane-Based Synthetic Approach", Science (1994) Vol 266 p 1961–1966, the contents of which are incorporated by this reference. For example "track-etch" polymeric or porous alumina membranes can be used as templates for nanotube preparation. The preparation of nanotubes by the "track-etch" process is described in examples 1 and 2.

Track-etch membranes prepared from polycarbonate and polyester are available from suppliers such as Osmonics (Minnetonka, Minn.) and Whatman (Maidstone, Kent UK) Track-etch membranes contain randomly distributed cylindrical pores of uniform diameter that run through the entire thickness of the membrane. Pore diameters as small as 10 nm are commercially available at pore densities of up to $10^9$ pores per square centimeter.

Porous alumina membranes, which are commercially available from Whatman (Maidstone, Kent UK), are prepared electronically from Al metal. Pore diameters as small as 5 nm can be achieved at pore densities as high as $10^{11}$ pores per square centimeter. Membranes can be prepared having the membrane thickness from as small as 100 nm to as large as 100 μm.

In addition, nanoparticles can be synthesized using templates prepared from glass (R. J. Tonucci et al., Science 258, 783 (1992)), xeolite (J. S. Beck et al., J. Am. Chem. Soc. 114, 10834 (1992)), and variety of other materials (G. A. Ozin, Adv. Mater. 4, 612 (1992)).

Nanotube Preparation

Nanotubes can be prepared within the membrane pores using electrochemical or chemical methods. Depending on the membrane and synthetic method used, the nanotubes may be solid or hollow. A wide variety of materials can be used to prepare such nanotubes. For example, nanotubes can be prepared from metals, polymers, semiconductors, carbons, or $Li^+$ intercalation materials. Metal nanotubes include those made from gold or silver. Semi-conductor nanotubes include those made from silicon or germanium. Polymer nanotubes include those made from biocompatible or biodegradable polymers, such as those described below. The nanotubes can be prepared from a single material. Alternatively, concentric tubular composite nanotubes can be prepared having an outer tube of one material surrounding an inner tube of another material.

The present invention allows for the preparation of nanotubes of controlled dimensions. Hence, the nanotube size can be specifically tailored to the problem at hand. For example, nanotubes can be prepared having a dimension optimized for the in-vivo delivery of a bioactive agent. In comparison, known biological drug delivery systems, such as viral vectors for delivery of genetic material, are hindered in their efficacy because their size cannot be altered and, hence, they have limited payload capabilities.

The ability to make nanotubes from a wide variety of materials or combination of materials allows the creation of nanotubes with desired biochemical properties such as biocompatibility, including immunogenic compatibility, and/or biodegradability. In comparison, certain biological drug delivery systems, such as viral vectors, can cause significant immunogenic phenomena.

Nanotube can also be synthesized such that both ends of the nanotube are open. Alternatively, solid nanotubes can be synthesized. Nanotubes of the present invention also include those synthesized such that one mouth of the nanotube is closed. Such nanotubes are advantageous because a cap need only be applied to the open end. Nanotubes with one closed end can also be produced by template synthesis. Before the alumina template membrane is removed from the substrate aluminum surface, the pores in the alumina terminate into a non-porous alumina barrier layer (Hornyak, G. L.; Patrissi, C. J.; Martin, C. R. "Fabrication, Characterization and Optical Properties of Gold-Nanoparticle/Porous-Alumina Composites: The Non-Scattering Maxwell-Garnett Limit," J. Phys. Chem B., 1997, 101, 1548–1555). This non-porous barrier layer is removed when the alumina membrane is stripped off the aluminum surface. However, if template synthesis is completed before removal of the alumina from the aluminum, the bottoms of the nanotubes are closed. Dissolution of the alumina then liberates the nanotubes that are closed a one end and open at the other end.

Preferred nanotubes are those comprising silica or polymers. Silica nanotubes can be prepared using sol-gel template synthesis as described in Lakshmi, B. B.; Patrissi, C. J.; Martin, C. R., "Sol-Gel Template Synthesis of Semiconductor Oxide Micro- and Nanostructures," *Chem. Mater.*, 1997, 9, 2544–2550; Lakshmi, B. B.; Dorhout, P. K.; Martin, C. R. "Sol-Gel Template Synthesis of Semiconductor Nanostructures," *Chem. Mater.*, 1997, 9, 857–862, the contents of which are incorporated by this reference. Here the template membrane is immersed into a standard tetraethylorthosilicate sol so that the sol fills the pores. After the desired immersion time, the membrane is removed, dried in air and then cured at 150° C. This yields silica nanotubes lining the pore walls of the membrane plus silica surface films on both faces of the membrane. The surface films are removed by briefly polishing with slurry of alumina particles. The nanotubes are then liberated by dissolving the template membrane and collected by filtration.

The outside diameter of the nanotube can be controlled by varying the pore diameter of the template membrane, the length of the nanotube can be controlled by varying the thickness of the template membranes, and the inside diameter of the nanotube can be controlled by varying the immersion time in the sol. The template membrane pore diameter can be varied to produce nanotubes having diameters from as small as 5 nm to as large as 100 μm. Likewise, the template membrane thickness can be varied to give nanotubes having a length from as small as 5 nm to as large as 100 μm.

The preferred dimensions of the nanotube depend on the intended application. When the nanotube is intended for in-vivo use, and particularly when the nanotube is to be injected into the blood stream, the maximum dimension of the nanotube is preferably less than 500 nm. The "maximum dimension" of the nanotube is the maximum distance between any two points in the nanotube. For a capped nanotube, containing a nanocap at each end, the maximum dimension is the maximum distance between any two points on the combined body.

Preferably, when the nanotube is intended for in-vivo use, the nanotube is of length less than 500 nm and diameter less than 200 nm. Especially preferred nanotubes for in-vivo use have a maximum dimension less than 100 nm. Because of concerns over occlusion of blood flow at the microvasculature level, it is important not to make nanoparticles too large for intravenous applications. For comparison purposes, a red blood cell is about 7000 nm in diameter, which corresponds to the diameter of the smallest capillaries in the human body. If the nanostructure complex has suitable surface property characteristics (surface charge and hydrophilicity/hydrophobicity balance) and has a dimension typically less than 10 nm, preferably 5 nm, it may be directly excreted from the body by the kidneys. On the other hand, if the nanostructure is larger and biodegradable, it won't be directly eliminated from the body (e.g., kidneys), but rather will be degraded into its smaller components, which in turn, are eliminated via the liver, kidney, bile, etc.

Polymer nanotubes can be prepared from many substances that are composed of monomer units. "Monomer units" are the individual moieties that are repeated to form "polymers". Multiple monomer units are covalently attached when in the form of a backbone of a polymer. Polymers that are made from at least two different types of monomer units are referred to as "copolymers". Polymerizing or copolymerizing describes the process by which multiple monomers are reacted to form covalently linked monomer units that form polymers or copolymers, respectively. A discussion of polymers, monomer units, and the monomers from which they are made may be found in Stevens, *Polymer Chemistry: An Introduction*, $3^{rd}$ ed., Oxford University Press, 1999, the contents of which are incorporated by this reference.

Polymeric nanotubes can be prepared using a solution deposition method as described in Cepak, V. M., Martin, C. R. "Preparation of Polymeric Micro- and Nanostructures Using a Template-Based Deposition Method", *Chem. Mater.*, 1999, 11, 1363–1367. This method entails depositing a solution of the desired polymer within the pores of the template membrane and allowing the solvent to evaporate. In addition, polymer nanotubes can be prepared by polymerizing a monomer within the pores as described by Martin, C. R., "Template Synthesis of Electronically Conductive Polymer Nanostructures," *Acc. Chem. Res.*, 1995, 28, 61–68.

Preferred polymers include polystyrene, polyorganosiloxane, poly(methyl methacrylate), polystyrene, polylactic acids, and other biodegradable polymers, acrylic latexes, polyorganosiloxane, cellulose, polyethylene, poly(vinyl chloride), poly(ethyl methacrylate), poly(tetrafluoroethylene), poly(4-iodostyrene/divinylbenzene), poly(4-vinylpyridine/divinylbenzene), poly(styrene/divinyl benzene), crosslinked melamine particles, phenolic polymer colloids, polyamide 6/6, natural rubber, naturally occurring biopolymers such as algenates, and collagen, or mixtures thereof.

When the nanotubes are to be introduced into an living organism, for example, when used as a vehicle for delivery of a bioactive material, biodegradable polymers and biocompatible polymers are especially preferred. A "biodegradable" substance is a substance that can be broken down by the action of living organisms. Examples of useful biodegradable polymers include polyesters, such as poly(caprolactone), poly(glycolic acid), poly(lactic acid), and poly(hydroxybutryate); polyanhydrides, such as poly(adipic anhydride) and poly(maleic anhydride); polydioxanone; polyamines; polyamides; polyurethanes; polyesteramides; polyorthoesters; polyacetals; polyketals; polycarbonates; polyorthocarbonates; polyphosphazenes; poly(malic acid); poly(amino acids); polyvinylpyrrolidone; poly(methyl vinyl ether); poly(alkylene oxalate); poly(alkylene succinate); polyhydroxycellulose; chitin; chitosan; and copolymers and mixtures thereof.

"Biocompatible" substances are substances that are compatible with and have no significant toxic effect on living organisms. Preferably, biocompatibility includes immunogenic compatibility. An "immunogenically compatible" substance is a substance that, when introduced into a body, does not significantly elicit humoral or cell-based immunity. Examples of biocompatible polymers include PLG [Poly (lactide-co-glycolide)], poly(ethylene glycol), copolymers of poly(ethylene oxide) with poly(L-Lactic acid) or with poly(β-benzyl-L-aspartate). In addition, a number of approaches can be used to make a nanotube surface biocompatible and "stealthy". For example, this can be accomplished by attaching a PEG-maleimide to the chain-end thiols on the outer surfaces of the nanotube. If the nanotube is composed of Au or similar metals, the PEG chain can be attached by a thiol linker as described in Yu, S.; Lee, S. B.; Kang, M.; Martin, C. R. "Size-Based Protein Separations in Poly(ethylene glycol)-Derivatized Gold Nanotubule Membranes," *Nano Letters*, 2001, 1, 495–498. Other examples of biocompatible polymers and surface treatments can be found in Majeti N. V. Ravi Kumar, "Nano and Microparticles as Controlled Drug Delivery Devices" J Pharm. Pharmaceut. Sci. 3(2): 234–258 (2000), the contents of which are incorporated by this reference.

Functionalization of the Nanotube Surface

Nanotubes can be prepared having different chemically or biochemically functionalized ends, and inner and outer surfaces. Methods used to functionalize a nanotube surface depend on the composition of the nanotube and are well known in the art. For example, functionalization of silica nanotubes is accomplished using silane chemistry. Here, different functional groups can be attached to the inside and outside surfaces of a nanotube by attaching a first group to the inner surface while the nanotubes are still embedded within the pores of the template. FIG. 1(A-E) shows such a process. Silica nanotubes are formed within the pores of a template membrane (FIG. 1(A-B)). Next, a hydrolytically unstable silane is reacted with surface silanol sites on the nanotube to obtain covalent, oxygen/silicon bonds between the surface and the silane (FIG. 1(C)). A second functional group is attached to the outer surface after dissolution of the template (FIGS. 1(D and E)).

Figure 3:
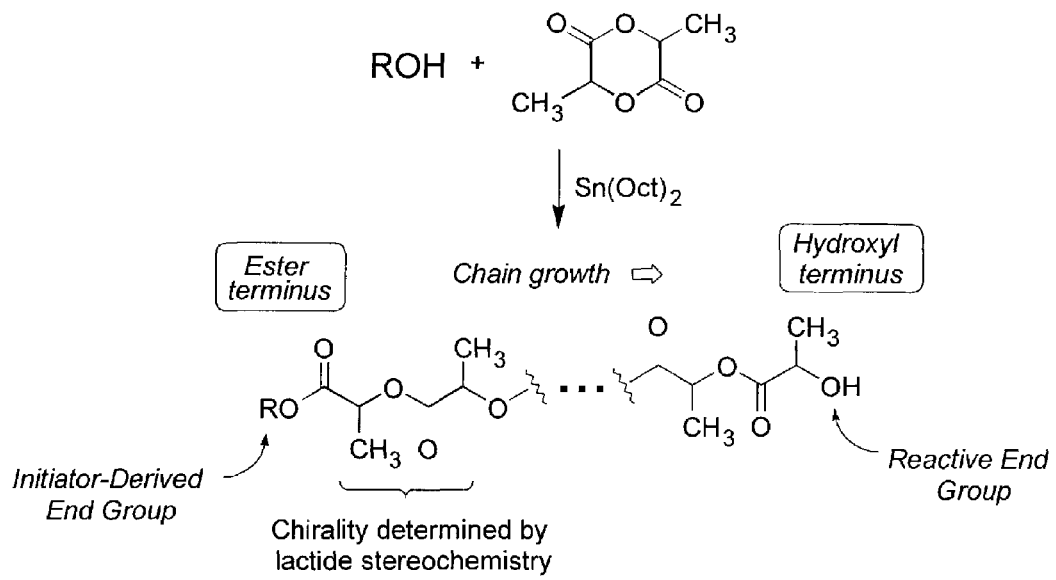
FIGS. 3(A)–(B) are schematic diagrams showing the preparation of endfunctionalized polylactides.
Figure 3:
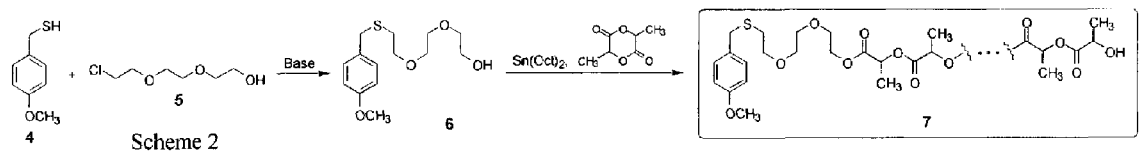

The surface of polymer nanotubes may also be functionalized using well-known chemical methods. For example, the methods employed for polylactide synthesis allow for differential end-functionalization. FIG. 3(A) shows such a method. Polymerization occurs by an insertion mechanism mediated by Lewis acids such as $Sn^{2+}$ whose bonds with oxygen have significant covalent character. An alcohol complexed with the metal ion initiates polymerization, which continues by stepwise ring-opening of the lactide monomers to generate a new alkoxide-metal complex capable of chain growth. The polymer molecular weight can be controlled by the molar ratio of initiating alcohol to the lactide monomer. The resulting polyester possesses directionality with a hydroxyl terminus (from the final monomer) and a functional group at the ester terminus determined by the structure of the initiating alcohol. The latter can contain a variety of functional groups.

In addition to having end-group functionality, functional groups can be introduced by copolymerization. Natural amino acids are sterically similar to lactic acid but offer a variety of functional groups on their side-chains (—OH, —$CO_2H$, —$NH_2$, —SH, etc.). Moreover, like lactic acid, -amino acids are found in all cell types, so that the polymer degradation products are non-toxic. Monomers derived from an -amino acid and lactic acid can be synthesized by standard methods and used for random copolymerization with lactide. Especially preferred nanotubes of the present invention are those having functional groups on a nanotube or nanocap surface. Such groups allow the nanotube/nanocap to be bioengineered to accomplish specific desired biomedical/biochemical functions.

Such particles allow for applications requiring of specific protein or cell immobilization. See Langer, R. "Tissue Engineering," Mol. Ther. 2000, 1, 12–15. Molecules, for example proteins, including antibodies or peptides, RNA or DNA aptamers, cellular receptors or cellular receptor ligands are attached to the nanotube/nanocap surface. Such molecules may be attached covalently, including attachment via functional groups introduced by functionalization of the surface. Alternatively, molecules may be covalently attached via linker molecules. Molecules may also be attached to the nanotube/nanocap surface by non-covalent linkage, for example by absorption via hydrophobic binding or Van der Waals forces, hydrogen bonding, acid/base interactions and electrostatic forces.

In addition, other suitable materials for drug delivery applications in biological systems can be incorporated into the nanotube-nanocap structural framework, which include but are not limited to chitosan, PEGylated PLGA (poly (lactic-co-glycolic acid)) and other PEGylated compounds. For example, a commercially available PEG-maleimide can be incorporated into the chain-end thiols on the outer surfaces of the nanotubes. "PEGylated" compounds are compounds modified by attaching PEG chains to the compounds.

Preparation of Capped Nanotubes

Nanoparticles having an outside diameter slightly larger than the inside diameter of the nanotubes can be used as nanocaps. Depending on the application, the capping nanoparticle is either prepared from the same material as the nanotube or, alternatively, is prepared from a different material. Methods of preparation of nanoparticles are well known in the art. For example, the preparation of monodisperse sol-gel silica nanospheres using the well-known Stober process is described in Vacassy, R. et al., "Synthesis of Microporous Silica Spheres", J. Colloids and Interface Science 2000, 227, 302.

Figure 2:
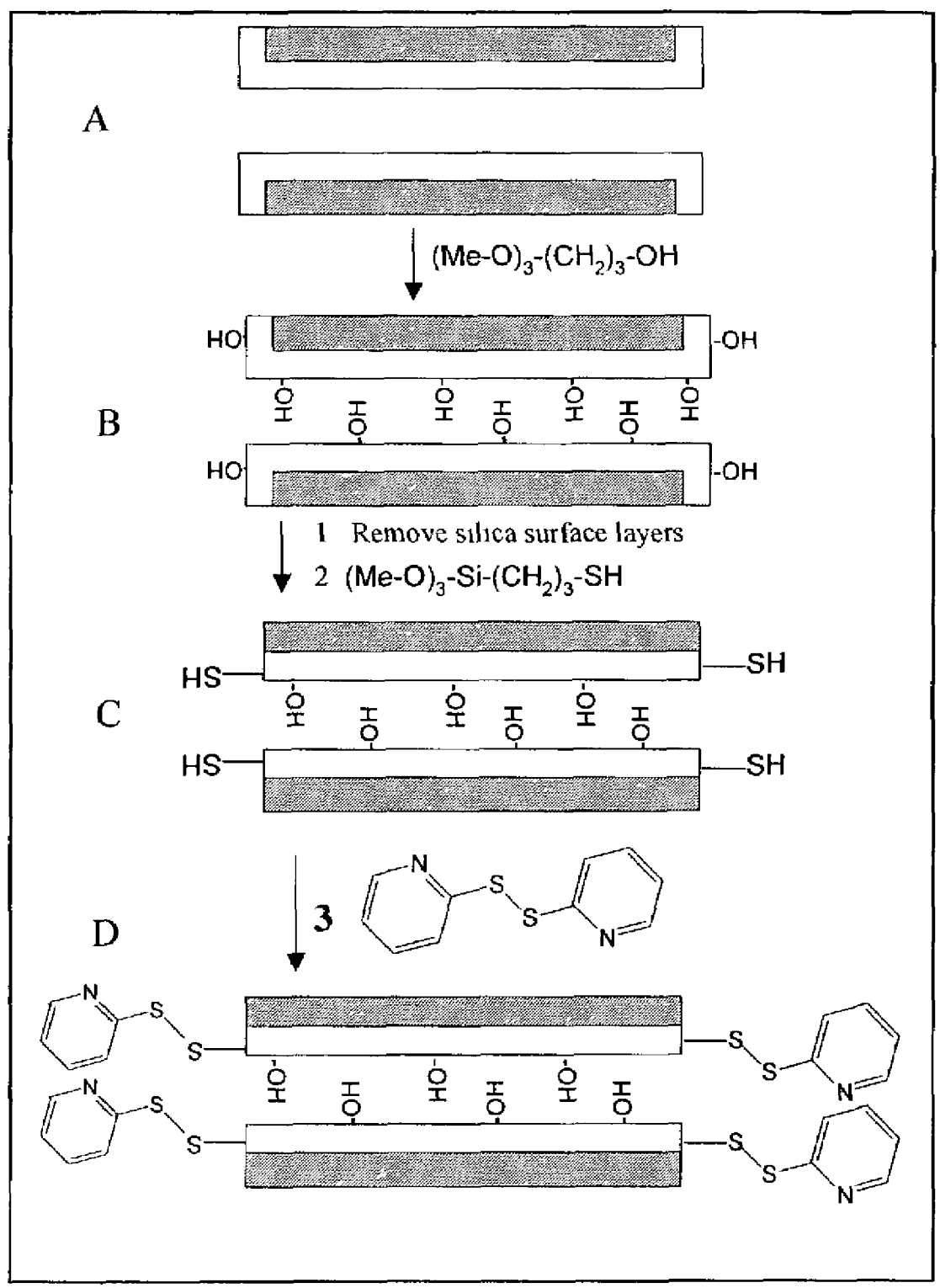
FIGS. 2(A)–(D) are schematic diagrams showing the disulfide activation of nanotube mouths.

A nanoparticle can be attached to the end of a nanotube by covalent bonds. For example, silica nanotubes and particles can be linked by disulphide bonds. FIG. 2(A-D) shows a method of preparing disulphide activated nanotube ends. Initially, the surface at the ends of silica nanotubes is functionalized with a —SH linker. This can be performed while the nanotubes are still embedded in the pores of the template membrane. This allows activation of the end surface without changing the chemical properties of the outer surface of the nanotubes.

If necessary, the inner surfaces of the nanotubes are protected with, for example, a silane group such as (Me—O)$_3$—(CH$_2$)$_3$—OH (FIG. 2(B)). After the protection step, the silica surface layers at the nanotube mouths are removed to expose fresh silica. The freshly-exposed silica will be reacted with the silane, such as (Me—O)$_3$—Si—(CH$_2$)$_3$—SH to attach the requisite —SH linker to the mouths of the nanotubes (FIG. 2(C)). The length of the alkyl chain in this silane can be varied to allow placement of the —SH linker any desired distance from the nanotube mouth. These —SH functionalities are then reacted with pyridine disulfide (3) in to obtain nanotubes with an activated disulfide bond at the nanotube ends (FIG. 2(D)).

The surface of the nanoparticles is functionalized with the same —SH containing silane used on the mouths of the nanotubes. Hence, nanotubes with an activated disulfide at their mouths and nanoparticles with an —SH group on their surface are available for linkage through disulfide bond formation.

Similar functionalization methods are applicable to nanotubes and nanoparticles prepared from materials other that silica, including biodegradable polymers. For example, the biodegradable polymer polylactide can be prepared using an sulfur-containing initiator to produce an initiator-derived protected thiol group at the ester terminus of the chain (see FIG. 3(B)). This group can be used to attach a nanoparticle cap via disulfide chemistry. Alternatively, higher —SH density can be achieved using the brush polymer approach to incorporate additional thiol groups (See Hrkach, J. S.; Ou, J.; Lotan, N.; Langer, R. "Synthesis of Poly(L-Lactic acid-co-L-lysine) Graft Copolymers," Macromolecules 1995, 28, 4736–4739).

Other types of covalent bonds, for example amide and ester bonds, can be used to attach the nanoparticle to the nanotube. Siloxane based linking can also be used. This would be particularly useful when the cap is composed of silica as the silanol sites on the silica surface react spontaneously with siloxanes to form a covalent oxygen-silicon bond. For metal nanotube or caps, thiol linkers can be used for attachment. For example the molecule(Me—O)$_3$—Si—(CH$_2$)$_3$—SH could be attached to a silica nanotube and a gold nanoparticle attached as the cap using the —SH end of this molecule. It is well known that such thiols form spontaneous As—S bonds with gold surfaces.

Figure 4:
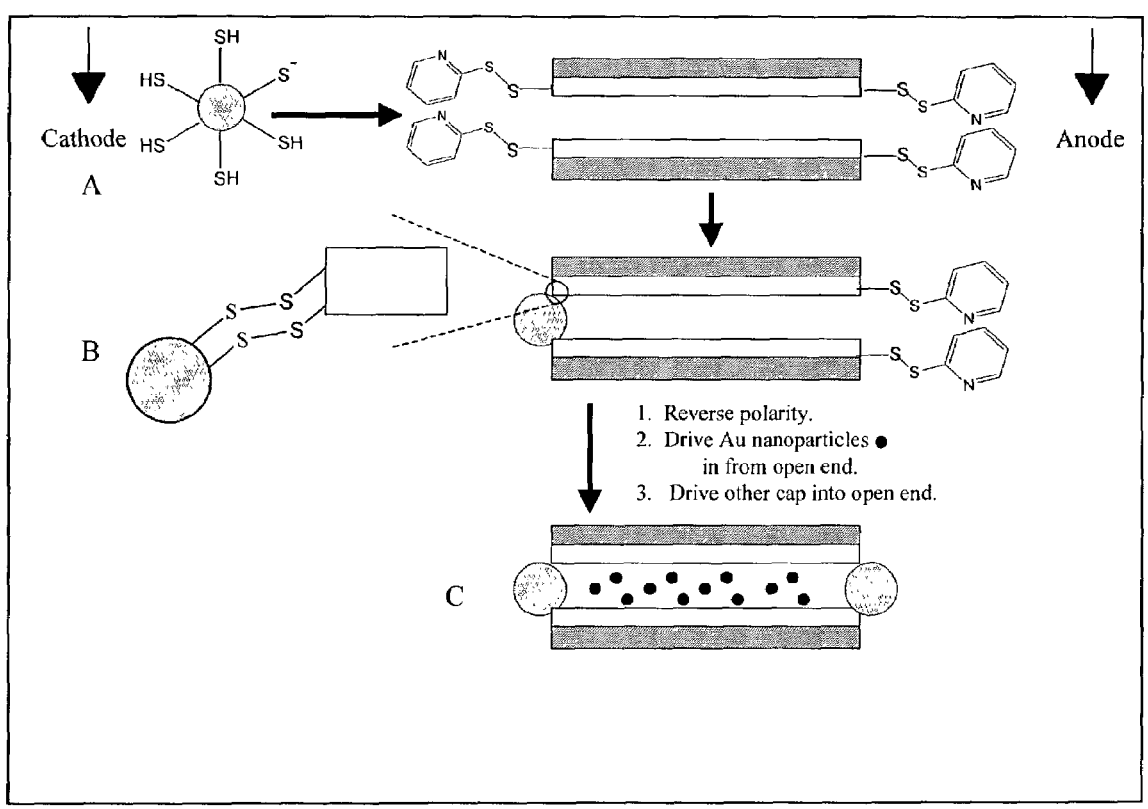
FIGS. 4(A)–(C) are schematic diagrams showing the loading and capping the nanotubes.

Nanoparticles can be electrophoretically placed within the mouths of nanotubes so that the entire mouth of the nanotube is blocked when disulfide bonds are formed between the nanotube and the nanoparticle as described in Miller, S. A. and Martin, C. R. "Electroosmotic Flow in Carbon Nanotube Membranes," *J. Am. Chem. Soc.,* 2001; 123(49); 12335–12342. For example, FIG. 4(A) shows a nanotube-containing membrane is mounted in a U-tube cell with Platinum electrodes immersed into the buffer solution on either side of the membrane. The —SH-functionalized nanoparticles are added to the cathode half-cell. The buffer solution is maintained at pH=7 so that a small fraction of the —SH groups on the nanoparticles are deprotonated. These negatively charged particles are driven into the mouths of the nanotubes electrophoretically by using the Platinum electrodes to pass a constant current through the membrane. Hence, the electrophoretic force causes the nanoparticles to nestle into the nanotube mouths, where disulfide bond formation will occur (FIGS. 4(B) and (C)).

As an alternative to the electrophoretic assembly method, —SH labeled nanocaps can be suspended in solution together with the activated disulfide labeled nanotubes. Here, the nanoparticle caps can spontaneously self-assemble to the nanotubes. The inventors have described the self-assembly of gold nanospheres and latex particles to template prepared polymeric and metal nanowires. (See Sapp, S. A.; Mitchell, D. T.; Martin, C. R. "Using Template-Synthesized Micro- and Nanowires as Building Blocks for Self-Assembly of Supramolecular Architectures," *Chem. Mater.* 1999, 11, 1183–1185.)

In addition to —SH linking, other covalent linking methods can be used to link nanotubes and nanoparticles. Non-covalent linking methods can also be used. These include, for example, DNA hybridization (Mirkin, C. A. "Programming the Self-Assembly of Two and Three-Dimensional Architectures with DNA and Nanoscale Inorganic Building Blocks," Inorg. Chem. 2000, 39, 2258–2272), the biotin/avidin interaction (Connolly, S.; Fitzmaurice, D. "Programmed Assembly of Gold Nanocrystals in Aqueous Solution," Adv. Mater. 1999, 11, 1202–1205), and antigen/antibody interactions (Shenton, W.; Davis, S. A.; Mann, S. "Directed Self-Assembly of Nanoparticles into Macroscopic Materials Using Antibody-Antigen Recognition," Adv. Mater. 1999, 11, 449).

Loading of Payloads into Nanotubes

Nanotube/nanocap combinations of the present invention can be used to deliver many different payloads or combinations of different payloads. The present invention includes the use of a nanotube/nanocap combination to deliver more than one payload agent contained within a single nanotube. For example, a combination of two or more bioactive reagents may be loaded into a single nanotube for delivery.

Specific payload bioactive agents include but are not limited to genetic material (e.g., DNA), RNA, oligonucleotides, peptides, proteins (e.g., enzymes), chemotherapeutics (anti-cancer drugs), antibiotics, antifungal agents, anesthetics, immunomodulators (e.g., interferon, cyclosporine), anti-inflammatory and other types of pain relieving drugs, autonomic drugs, cardiovascular-renal drugs, endocrine drugs, hematopoietic growth factors, blood lipid lowering drugs, AIDS drugs, modulators of smooth muscle function, antileptics, psychoactive drugs, and drugs that act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable agents may be selected from, for example, proteins, enzymes, hormones, polynucleotides, nucleoproteins, polysaccharides, glycoproteins, lipoproteins, polypeptides, steroids, analgesics, local anesthetics, antibiotic agents, anti-inflammatory corticosteroids, ocular drugs and synthetic analogs of these species.

Examples of drugs which may be delivered by nanotubes include, but are not limited to, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperzine maleate, anisindone, diphenadione erythrityl tetranitrate, digoxin, isoflurophate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-S-estradiol, ethinyl estradiol, ethinyl estradiol 3-methyl ether, prednisolone, 17-α-hydroxyprogesterone acetate, 19-norprogesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, mandol, quanbenz, hydrochlorothiazide, ranitidine, flurbiprofen, fenufen, fluprofen, tolmetin, alclofenac, mefenamic, flufenamic, difuinal, nimodipine, nitrendipine, nisoldipine, nicardipine, felodipine, lidoflazine, tiapamil, gallopamil, amlodipine, mioflazine, lisinolpril, enalapril, enalaprilat captopril, ramipril, famotidine, nizatidine, sucralfate, etintidine, tetratolol, minoxidil, chlordiazepoxide, diazepam, amitriptyline, and imipramine. Further examples are proteins and peptides which include, but are not limited to, bone morphogenic proteins, insulin, colchicine, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, GRF, somatostatin, lypressin, pancreozymin, luteinizing hormone, LHRH, LHRH agonists and antagonists, leuprolide, interferons such as interferon alpha-2a, interferon alpha-2b, and consensus interferon, interleukins, growth hormones such as human growth hormone and its derivatives such as methione-human growth hormone and des-phenylalanine human growth hormone, bovine growth hormone and porcine growth hormone, fertility inhibitors such as the prostaglandins, fertility promoters, growth factors such as insulin-like growth factor, coagulation factors, human pancreas hormone releasing factor, analogs and derivatives of these compounds, and pharmaceutically acceptable salts of these compounds, or their analogs or derivatives.

Other bioactive agents, which may be delivered by nanotubes, include chemotherapeutic agents, such as carboplatin, cisplatin, paclitaxel, BCNU, vincristine, camptothecin, etopside, cytokines, ribozymes, interferons, oligonucleotides and oligonucleotide sequences that inhibit translation or transcription of tumor genes, functional derivatives of the foregoing, and generally known chemotherapeutic agents such as those described in U.S. Pat. No. 5,651,986.

Nanotube-nanocap combinations can be efficiently and cheaply loaded with payloads, offering a significant advantage over nanoparticle based delivery systems. For example, charged payload agents may be loaded using an electrophoretic force. (See Miller, S. A.; Martin, C. R. "Electroosmotic Flow in Carbon Nanotube Membranes," *J. Am. Chem. Soc.*, 2001; 123(49); 12335–12342.) FIGS. 4(B) and (C) show the loading of nanotubes with gold nanoparticles by using electrophoretic force to drive the gold nanoparticles through the open ends of nanotubes. After loading the open ends can be sealed with —SH-functionalized nanocaps.

Alternatively, nanotubes embedded within the synthesis membrane are closed or capped at one end and filled with the desired payload by vacuum filtering a solution of the agent through the membrane. (R. Parthasarathy and C. R. Martin, *Nature* 369, 298 (1994).)

Nanotubes that are closed on one end can be prepared by forming the tubes in an alumina template film prior to removal of the alumina from the underlying aluminum surface. Nanotubes of this type can be filled by simply applying a solution of the payload to the surface of the film (where the open ends of the tubes are located) and allowing the solvent to evaporate. Multiple applications can be used, if needed.

Controlled Delivery of Bioactive Agents Using Nanotubes

Nanotube technology provides a method for delivering bioactive agents (e.g., DNA) to living cells. In one embodiment, this is achieved using nanocaps that are firmly bound to the nanotube when the assembly is outside of the cell but are released, thus opening the nanotube and making the bioactive agent available, when the assembly is partitioned into the cell. For example, this can be accomplished using disulfide chemistry to couple the nanoparticle cap to the nanotube. The disulfide link between the nanotube and its nanocap is ideal because all living cells maintain a reducing environment within their cytoplasm. This contrasts with the oxidizing environment found outside the cell. The tripeptide glutathione (-gluatamyl-cysteinyl-glycine) plays a key role in this process. In its reduced form, glutathione possesses a free sulfhydryl capable of reducing disulfide bonds, forming a disulfide-linked glutathione dimer in the process. This species, in turn, is reduced by nicotinamide-dependent enzymes.

The overall effect is to ensure that any sulfhydryls in the cytoplasm are maintained in a reduced (free —SH) form. Because of the high reactivity of glutathione toward disulfide bonds, no enzymes are required to catalyze disulfide reduction. Because of this unique intercellular chemistry, the disulfide linkages holding the nanoparticles caps to the nanotube are broken once the nanotube enters the cell, making the bioactive agent immediately available for delivery.

Nanotubes with non-releasable caps also provide a method of controlled release of bioactive agents. For example, nanotubes may be prepared using biodegradable materials, for example, the biodegradable polymers discussed above, which degrade after a fixed time and release their payload. Alternatively, nanotubes can be prepared from materials of limited permeability, resulting in the release of the bioactive agent over a controlled time period. Nanotubes can also be prepared using materials that swell after a fixed time, resulting in increased diffusion of the nanotube contents.

Pharmaceutical Compositions Comprising a Nanotube Delivery System

A nanotube delivery system of the present invention can be incorporated into pharmaceutical compositions. Such compositions typically comprise the nanotube delivery system, including a bioactive payload, and a pharmaceutically acceptable carrier. A "pharmaceutically acceptable carrier" includes any and all solvents, dispersion media, coatings, antibacterial and antifungal agents, isotonic and absorption delaying agents, and the like, compatible with pharmaceutical administration (Gennaro, A. R. 2000. Remington: The science and practice of pharmacy. Lippincott, Williams & Wilkins, Philadelphia, Pa.). Preferred examples of such carriers or diluents include, but are not limited to, water, saline, Finger's solutions, dextrose solution, and 5% human serum albumin. Liposomes and non-aqueous vehicles such as fixed oils may also be used. Except when a conventional media or agent is incompatible with an active compound, use of these compositions is contemplated. Supplementary active compounds can also be incorporated into the compositions.

A pharmaceutical composition of the nanotube delivery system is formulated to be compatible with its intended route of administration, including intravenous, intradermal, subcutaneous, oral (e.g., inhalation), transdermal (i.e., topical), transmucosal, and rectal administration. Solutions or suspensions used for parenteral, intradermal, or subcutaneous application can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid so as to be administered using a syringe. Such compositions should be stable during manufacture and storage and must be preserved against contamination from microorganisms such as bacteria and fungi. The carrier can be a solvent or dispersion medium containing, for example, water, ethanol, polyol (such as glycerol, propylene glycol, and liquid polyethylene glycol), and suitable mixtures. Proper fluidity can be maintained, for example, by using a coating such as lecithin, by maintaining the required particle size in the case of dispersion and by using surfactants. Various antibacterial and antifungal agents, for example, parabens, chlorobutanol, phenol, ascorbic acid, and thimerosal, can contain microorganism contamination. Isotonic agents, for example, sugars, polyalcohols such as manitol, sorbitol, and sodium chloride can be included in the composition. Compositions that can delay absorption include agents such as aluminum monostearate and gelatin.

Sterile injectable solutions can be prepared by incorporating the nanotube delivery system in the required amount in an appropriate solvent with one or a combination of ingredients as required, followed by sterilization. Generally, dispersions are prepared by incorporating the nanotube delivery system into a sterile vehicle that contains a basic dispersion medium, and the other required ingredients. Sterile powders for the preparation of sterile injectable solutions, methods of preparation include vacuum drying and freeze-drying that yield a powder containing the active ingredient and any desired ingredient from a sterile solutions.

Oral compositions generally include an inert diluent or an edible carrier. They can be enclosed in gelatin capsules or compressed into tablets. For the purpose of oral therapeutic administration, the nanotube delivery system can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or STEROTES; a glidant such as colloidal silicon dioxide; a sweetening agent such as sucrose or saccharin; or a flavoring agent such as peppermint, methyl salicylate, or orange flavoring.

For administration by inhalation, the compounds are delivered as an aerosol spray from a nebulizer or a pressurized container that contains a suitable propellant, e.g., a gas such as carbon dioxide.

Systemic administration can also be transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the nanotube delivery system is formulated into ointments, salves, gels, or creams.

The compounds can also be prepared in the form of suppositories (e.g., with bases such as cocoa butter and other glycerides) or retention enemas for rectal delivery.

In one embodiment, the active compounds are prepared with carriers that protect the nanotube delivery system against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Polyethylene glycols, e.g. PEG, are also good carriers. Such materials can be obtained commercially from ALZA Corporation (Mountain View, Calif.) and NOVA Pharmaceuticals, Inc. (Lake Elsinore, Calif.), or prepared by one of skill in the art. Liposomal suspensions can also be used as pharmaceutically acceptable carriers. These can be prepared according to methods known to those skilled in the art, such as in (Eppstein et al. U.S. Pat. No. 4,522,811. 1985).

Oral formulations or parenteral compositions in unit dosage form can be created to facilitate administration and dosage uniformity. Unit dosage form refers to physically discrete units suited as single dosages for the subject to be treated, containing a therapeutically effective quantity of bioactive agent/nanotube delivery system in association with the required pharmaceutical carrier. The specification for the unit dosage forms of the invention are dictated by, and directly dependent on, the unique characteristics of the bioactive agent and the particular desired therapeutic effect, and the inherent limitations of compounding the bioactive agent.

The nanotube delivery system of the present invention can be used as a gene therapy delivery mechanism. Gene therapy compositions can be delivered to a subject by, for example, intravenous injection, local administration (Nabel and Nabel, U.S. Pat. No. 5,328,470, 1994), or by stereotactic injection (Chen et al., Gene therapy for brain tumors: regression of experimental gliomas by adenovirus-mediated gene transfer in vivo. *Proc Natl Acad Sci USA.* 91:3054–7 (1994)). The pharmaceutical preparation of a gene therapy delivery mechanism can include an acceptable diluent, or can comprise a slow release matrix in which the gene delivery vehicle is imbedded.

The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Kits

The invention also provides kits containing one or more of the following in a package or container: (1) a composition comprising a bioactive agent contained in a nanotube delivery system of the present invention; (2) a pharmaceutically acceptable adjuvant or excipient; (3) a vehicle for administration, such as a syringe or catheter; (4) instructions for administration. Embodiments in which two or more of components (1)–(4) are found in the same container are also contemplated.

When a kit is supplied, the different components of the composition may be packaged in separate containers and admixed immediately before use. Such packaging of the components separately may permit long-term storage without losing the active components' functions.

The reagents included in the kits can be supplied in containers of any sort such that the life of the different components are preserved and are not adsorbed or altered by the materials of the container. For example, sealed glass ampules may contain lyophilized nanotubes, or buffers that have been packaged under a neutral, non-reacting gas, such as nitrogen. Ampules may consist of any suitable material, such as glass, organic polymers, such as polycarbonate, polystyrene, etc.; ceramic, metal or any other material typically employed to hold similar reagents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc. Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

A more complete understanding of the present invention can be obtained by reference to the following specific Examples. The Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations. Modifications and variations of the invention as hereinbefore set forth can be made without departing from the spirit and scope thereof, and, therefore, only such limitations should be imposed as are indicated by the appended claims.

EXAMPLE 1

Preparation of Silica Nanotubes

Porous alumina membranes having pore diameters of 200 nm and a thickness of 60 μm were obtained from Whatman (Maidstone, Kent UK). The membranes had a pore density of ~$\mathbf{10}^{10}$ pores per square centimeter.

Silica nanotubes were prepared by the sol-gel method as described by Brinker and Scherer (C. J. Brinker, G. W. Scherer, *Sol-gel Science,* Academic Press Inc., New York, 1990). Briefly, tetraethoxysilane (Aldrich, Milwaukee, Wis.)

was allowed to condense to form a suspension of fine colloidal particles (the sol). The template membrane was then immersed into the sol for 20 minutes to apply a thin layer of sol to the walls of the pores. The membrane was then removed, dried in air and then heated at 150 degrees C. for 5 hours to gel the sol and ultimately to condense the gel (by loss of water) to silica. This process yields silica nanotubes lining the pore walls plus silica surface films on both faces of the membrane.

The surface films were removed by briefly polishing with a slurry of alumina particles using standard 1 micron alumina polishing powder; hand polishing was done for approximately 2 mins. on each side. The nanotubes were then liberated from the template membrane by placing the membrane in $10^{-3}$ M NaOH for 60 minutes to dissolve the membrane. The nanotubes were collected by filtration using a microporous polycarbonate track-etched filter (pore diameter 30 nm) and stored in air.

EXAMPLE 2

Preparation of Polymeric Nantubes (a) Polystyrene nanotubes were prepared as described by Cepak et al. "Preparation of Polymeric Micro- and Nanostructures Using a Template-Based Deposition Method", *Chem. Mater.*, 1999, 11, 1363–1367. Briefly, a 5 wt % solution of polystyrene (M. Wt. 5000, Polysciences) was prepared in $CH_2Cl_2$, and approximately 1 mL of this solution was applied to the surface of a commercially available track-etched polyester membrane (Nuclepore, 30 nm-diameter pores, Whatman, Maidstone, Kent UK). Vacuum (from a water aspirator) was used to filter this solution through the pores of the membrane. This resulted in deposition of a thin layer of polymer on the pores walls. The solvent was then allowed to evaporate at room temperature in air for 6 hours. The template membrane was then dissolved by immersion in hexafluoro-2-propanol (Aldrich, Milwaukee, Wis.) with stirring for 10 hours. The liberated nanotubes were collected by filtration onto a 20 nm-pore diameter nanopore alumina filter (Whatman). The nanotubes were rinsed with the hexafluoro-2-propanol to remove excess polyester.

(b) Polyaniline nanotubes were prepared as described by Martin "Template Synthesis of Electronically Conductive Polymer Nanostructures," *Acc. Chem. Res.*, 1995, 28, 61–68. This method entails polymerization of the monomer with the pores of the template to form the polymer nanotubes on the pore walls.

The template membrane used was a track-etched polycarbonate membrane (Nuclepore) with 100 nm diameter pores. This membrane was immersed into a solution of 0.325 M aniline (Aldrich, Milwaukee, Wis.) in 1 M HCl. An equal volume of an oxidant solution (sodium vanadate, (Aldrich, Milwaukee, Wis.) 0.125 M, and p-toluene sulfonic acid (Aldrich, Milwaukee, Wis.) 0.5 M), also dissolved in 1 M HCl, was added with stirring. The mixture was polymerized for two hours. Polyaniline deposited on the pore walls to make polyaniline nanotubes within the pores. The surface polyaniline layers were removed by polishing as described in Example 1. The membrane was then immersed into dichloromethane for 4 hours with stirring to dissolve the polycarbonate template. The liberated nanotubes were collected by filtration onto a 20 nm-pore diameter nanopore alumina filter (Whatman). The nanotubes were rinsed with the dichloromethane to remove excess polycarbonate. Further details can be found in Parthasarathy, R. V.; Martin, C. R. *Chem. Mat.* 1994, 6, 1627–1632.

EXAMPLE 3

Preparation of Capped Nanotubes (Prophetic Example)

Monodisperse silica microspheres are prepared as described by W. Stöber et al., *J Colloid Interface Sci.* 1968, 26, 62–69. Briefly, 0.2 M tetraethylorthosilicate (Fisher, Fairlawn, N.J.) is precipitated in a mixture of ethanol, aqueous 0.2 M ammonia (Fisher, Fairlawn, N.J.) and 3.2M water. Surface sulfhydryl groups are introduced by including 3-mercaptopropyltrimethoxysilane (Aldrich, Milwaukee, Wis.) as described by J. S. Lee, S. et al., *React. Funct. Polymers* 2001, 49, 159–172. The nanosphere diameters are varied by adjusting reactant concentrations. Preferably, nanospheres having diameters approximately 30% larger than those of the nanotubes are preferred.

Silica nanotubes was prepared as in Example 2. The open ends of the nanotubes are functionalized with surface thiol groups while still embedded within the template membrane. Surface silanol groups are exposed by brief polishing the membrane with alumina particles. The exposed ends are then reacted with 3-mercaptopropyltrimethoxysilane (Aldrich, Milwaukee, Wis.). Reactive disulfides are produced by incubation with 2,2'-dipyridyl disulfide (Aldrithiol®, Aldrich, Milwaukee, Wis.).

The free sulfhydryl groups on the nanocaps react with the activated disulfide bonds on the mouths of the nanotubes to covalently join these structures. The complementary functionalities prevent formation of nanotube—nanotube or cap—cap dimers. To ensure that the nanocaps form a tight seal at the mouths of the nanotubes, the nanotube-containing membrane is mounted in a U-tube with Pt electrodes immersed into the buffer solution on either side of the membrane. The thiol-functionalized nanocaps are added to the cathode half-cell which contains a buffer at pH 7, which ensures that a fraction of the SH groups are deprotonated and thereby endows the nanocaps with an overall negative charge. Current is then passed through the system, electrophoretically driving the caps onto the membrane containing the nanotubes where the disulfide interchange reaction occurs and covalently links the structures. The system is then reversed to cap the remaining open end of the nanotube in the same manner.

EXAMPLE 4

Preparation of Nanotubes Containing a Chemically Attached Bioreactive Molecule

The Fab fragment of antibodies specific for the drug 4-[3-(4-fluorophenyl)-2-hydroxy-1-[1,2,4]triazol-1-yl-propyl]-benzonitrile was prepared as described by Nevanen, T. K. et al., J Chromatogr. A 025 89 (2001).

Freshly made $SiO_2$-nanotube-containing alumina membranes, were prepared as in Example 1. Nanotubes with antibody attached to both the inside and outside surfaces were prepared as follows: The nanotubes were first liberated from the membrane by dissolution of the template and collected by filtration. The membrane was dissolved by immersion into 25% phosphoric acid for 5 hours. The liberated nantubes were then immersed for 6 hours in an ethanol-based solution that was 5% in aqueous acetate buffer, 10% in trimethoxysilylpropyl aldehyde (PSX1050, United Chemical Technologies), pH was adjusted to 5.0. The resulting aldehyde-modified nanotubes were then collected by filtration, rinsed with ethanol, and dried for 24 hours in an Ar-filled (oxygen free) glove box.

The aldehyde-modified nanotubes were incubated overnight at 4° C. and then 1 day at room temperature with a solution of the Fab antibody fragment in pH=7 phosphate buffer (approximately 2 mg antibody/ml buffer). The antibody-modified nanotubes were then collected again and thoroughly rinsed with buffer solution.

Nanoparticles having antibody attached to only the inner surface were prepared as follows: While still within the pores of the template membrane, the inner surfaces of the nanotubes were treated with aminopropyltrimethoxysilane (United Chemical Technologies) using the solution-based method described above for aldehyde silane.

The template membrane was then dissolved as described above and the amino sites on the inner surfaces were coupled to free amino groups on the Fab fragment using the well-known glutaraldehyde coupling reaction. This was accomplished by immersing the nanotubes into a glutaraldehyde solution for 2 hrs, rinsing, collecting by filtration and immersing into a solution containing the antibody fragment, as described above.

EXAMPLE 5

Functionalization of the Nanotube Surface

Silica nanotubes where prepared as in example 1. However, before the nanotubes were released from the template, the internal surface of the nanotubes was functionalized. Functionalization was performed using standard saline chemistry as described in the previous examples. Briefly, a hydrolytically unstable silane was reacted with surface silanol sites on the nanotubes to obtain covalent oxygen/silicon bonds between the surface and the silane. The green fluorescent silane N-(triethoxysilylpropyl)dansylamide (United Chemical Technologies) was then attached to the inside surface of the nanotube using the method of Mitchell, D. T. et al., "Smart Nanotubes for Bioseparations and Biocatalysis" J. Am. Chem. Soc. 2002, 124, 11864–11865.

The nanotubes were immersed into an ethanol-based solution of 5% aqueous acetate buffer, 10% green fluorescent silane, pH 5.0 for 6 hours. The nanotubes were then collected by filtration and rinsed with ethanol.

The template membrane was dissolved to release the nanotubes as in example 1. The nanotubes were then added to a vial containing 10 ml water and 10 ml of cyclohexane. The vial was shaken vigorously and the two phases allow to settle. The green fluorescence of the silane N-(triethoxysilylpropyl)dansylamide was detected only in the lower aqueous phase containing the hydrophilic silica nanotubes.

The inner surface of second set of nanotubes were functionalized as above. However, here the blue fluorescent silane triethoxysilylpropylquinineurethan (Aldrich, Milwaukee, Wis.) was used. The reaction conditions were as described above for N-(triethoxysilylpropyl)dansylamide. After release from the membrane, hydrophobic octadecyl silane (C18) (Aldrich, Milwaukee, Wis.) was attached to the exterior surfaces of these nanotubes. The reaction conditions were as described above.

When the second set of nanotubes were added to the water/cyclohexane mixture, blue fluorescence, indicative of triethoxysilylpropylquinineurethan, was observed only in the cyclohexane phase containing the nanotubes having a hydrophobic exterior surface.

EXAMPLE 6

Release of Nanoparticle Payload (Prophetic Example)

Controlled uncapping of capped nanotubes can be demonstrated by using a protease assay described by Gulnik et al., FEBS Lett. 1997, 413, 379–384.

Capped nanotubes are prepared as in Example 3. A doubly-fluorescent labeled peptide is incorporated as the "payload" inside the capped nanotube. The peptide—acetyl-Glu-Glu-(γ-EDANS-Glu)-Lys-Pro-Ile-Cys-Phe-Phe-Arg-Leu-Gly-(Nε-DABCYL-Lys)-Glu-NH$_2$—contains a fluorophore (EDANS, 5-([2-aminoethyl)amino]napthalene-1-sulfonic acid) and a fluorescence quencher (DABCYL, (4-(4-dimethylaminophenylazo) benzoic acid) (Molecular Probes, Eugene Oreg.). The payload is incorporated by first capping one end of the nanotube. A solution containing the payload is then added to the open end of the nanotube. The open end of the nanotube is then capped as described in Example 3. The nanotubes are then released from the membrane as described in Example 1.

Because the two fluorescent compounds are covalently joined to the same peptide, intramolecular fluorescence resonant energy transfer (FRET) results in a very low fluorescence signal. However, when the peptide is cleaved by the protease cathepsin D (Sigma, St. Louis, Mo.), the fluorophore and quencher diffuse away from one another, which eliminates the FRET and leads to a high fluorescence.

To demonstrate uncapping in the presence of a reducing environment, the disulfide-linked, capped nanotube containing the labeled peptide is placed in a buffer solution containing cathepsin D. Dithiothreitol is added to a final concentration of 5 mM, then the fluorescence of the sample is measured as a function of time (excitation wavelength 349 nm, emission wavelength 487 nm). A control experiment in which the thiol reducing agent is omitted demonstrates that cathepsin D is unable to penetrate the covalently-capped nanotube (as shown by the negligible fluorescence increase under these conditions).

EXAMPLE 7

Experiments Using Nanoparticles in Mammalian (Human) Cells

Fluorescently-labeled silica nanotubes were prepared as in Example 5. The fluorescent dye was bound to the inner surface on the nanotubes. The outer surfaces of the nanotubes were functionalized by covalently binding antibodies to the human endothelial cell surface protein, intercellular adhesion molecule 1 (ICAM-1) (R & D Systems, Minneapolis, Minn.) using the method described in Example 4. Silica fluorescent nanotubes having no antibody attached were used as controls.

Human umbilical vein endothelial cells (HUVECs) (obtained from ATCC (American Type Culture Collection—ATCC Number CRL-1730) were grown as monolayers in EGM (Endothelial Cell Medium with 2% fetal bovine serum, growth factors, antibiotic-antimycotic, and supplements from Clonetics and BioWhittaker Corporation, Walkersville, Md.) at 37° C. in humidified air and 5% CO$_2$ on poly-L-lysine coated sterile 35 mm tissue culture plates (MatTek Corporation, Ashland, Mass.) containing a glass coverslip bonded to the bottom of the plate for viewing cells under a fluorescent microscope. When the cells were approximately 80–90% confluent, the nanotube experiments were conducted.

Nanotubes for the experiments were approximately 50 nM wide and 300 nM long. Equal amounts of serially-diluted fluorescently-labeled nanotubes (either control or antibody-labeled) were incubated in 2 mL of phenol red-free medium on the HUVECs for 30 to 60 minutes prior to washing with phosphate-buffered saline solution and replacing the nanotube-containing medium with phenol red-free medium not containing nanotubes. Within one hour of exposure to the nanotubes, the cells were viewed under a Zeiss Axioplan fluorescent microscope. The best fluorescent images were obtained from experiments with 100- and 1000-fold dilution of the stock nanotube preparations (both control and ICAM-1-labeled). With the Zeiss Axioplan fluorescent microscope, we observed a 10–20 fold increase in fluorescence per high-power field (~50 cells/field) of HUVECs exposed to ICAM-1-labeled nanotubes compared to control HUVECs exposed to nanotubes without antibody labeling.

Using Bio-Rad 1024ES Confocal laser scanning fluorescent microscope to further visualize HUVECs with antibody-labeled nanotubes, and unlabeled nanotubes as a control, we observed that a 5-fold greater amount of the fluorescence was within the cells of the ICAM-1-labeled nanotube-treated HUVECs per high power field compared to control HUVECs, indicating that not only do the ICAM-1-labeled nanotubes have a much higher propensity to bind to HUVECs compared to control, but the nanotubes are actually internalizing into the cells.

We claim:

1. A nanotube comprising:
   (a) a hollow tubular body defining an inner void, comprising a first end and a second end, wherein the first end is open; and
   (b) a first end cap positioned over the first open end, wherein the end cap is attached to the hollow tubular body by a covalent bond and the capped nanotube has a maximum dimension of less than 100 µm.

2. The nanotube of claim 1, wherein the second end is open and a second end cap is positioned over the second open end, wherein the second end cap is attached to the hollow tubular body by a covalent bond.

3. The nanotube of claim 1, wherein the second end is closed.

4. The nanotube of claim 1, wherein the maximum dimension of the nanotube is less than 500 nm.

5. The nanotube of claim 4, wherein the diameter of the nanotube is less than 200 nm.

6. The nanotube of claim 5, wherein the maximum dimension of the nanotube is less than 100 nm.

7. The nanotube of claim 1, wherein a diameter of the tubular body is greater than 5 nm.

8. The nanotube of claim 1, wherein the tubular body comprises materials selected from a group consisting of a polymer, a semiconductor, carbon, Li+intercalation materials, and silica.

9. The nanotube of claim 8, wherein the tubular body comprises a polymer.

10. The nanotube of claim 9, wherein the polymer is biodegradable.

11. The nanotube of claim 9, wherein the polymer is biocompatible.

12. The nanotube of claim 10, wherein the polymer is poly(lactic acid).

13. The nanotube of claim 8, wherein a surface of the tubular body is functionalized.

14. The nanotube of claim 13, further comprising a protein attached to the surface.

15. The nanotube of claim 14, wherein the protein is selected from a group consisting of an antibody, an antibody fragment, and a cellular receptor ligand.

16. The nanotube of claim 13, wherein an outer surface of the tubular body is functionalized.

17. The nanotube of claim 1, further comprising a payload, wherein the payload fills the inner void of the tubular body.

18. The nanotube of claim 17, wherein the payload is a bioactive agent.

19. The nanotube of claim 18, wherein the bioactive agent is selected from a group consisting of a nucleic acid, a chemotherapeutic, an immunosuppressant, an antibiotic, an endocrine drug, an antifungal agent, a cardiovascular drug, and a renal drug.

20. The nanotube of claim 1, wherein the covalent bond is a disulfide bond.

21. The nanotube of claim 1, wherein a biocompatible material is attached to an outer surface of the nanotube.

22. The nanotube of claim 21, wherein the biocompatible material is selected from a group consisting of PEGylated PLGA, PLGA, chitosan, and polylactic acid.

23. The nanotube of claim 22, wherein the biocompatible material is PEGylated PLGA.

24. A bioactive agent delivery system comprising:
   (a) a hollow tubular body defining an inner void, comprising a first end and a second end, wherein the first end is open;
   (b) a first end cap positioned over the first open end, wherein the end cap is attached to the hollow tubular body by a covalent bond;
   (c) a bioactive agent,
   wherein the bioactive agent is contained within the inner void and the hollow tubular body has a maximum dimension of less than 100 µm.

25. A nanotube delivery system comprising:
   (a) a hollow tubular body defining an inner void, comprising a first open end and a second open end; and
   (b) a bioactive agent attached to a surface of the hollow tubular body by a covalent or non-covalent bond, wherein the hollow tubular body has a maximum dimension of less than 100 µm.

26. The delivery system of claim 25, wherein the maximum dimension is less than 500 nm.

27. The delivery system of claim 26, wherein the maximum dimension is less than 100 nm.

28. The delivery system of claim 25, wherein the hollow tubular body comprises materials selected from a group consisting of a polymer, a semiconductor, carbon, Li+intercalation materials, and silica.

29. The delivery system of claim 28, wherein the hollow tubular body comprises a polymer.

30. The delivery system of claim 29, wherein the polymer is biodegradable.

31. The delivery system of claim 29, wherein the polymer is biocompatible.

32. The delivery system of claim 25, wherein the bioactive agent is selected from the group consisting of DNA, oligonucleotides, chemotherapeutics, antibiotics, antifungal agents, anesthetics, immunomodulators, anti-inflammatory drugs, pain relieving drugs, autonomic drugs, cardiovascular-renal drugs, endocrine drugs, hematopoietic growth factors, blood lipid lowering drugs, AIDS drugs, modulators of smooth muscle function, antileptics, and psychoactive drugs.

33. The delivery system of claim 24, wherein the bioactive agent is selected from the group consisting of DNA, oligonucleotides, chemotherapeutics, antibiotics, antifungal agents, anesthetics, immunomodulators, anti-inflammatory drugs, pain relieving drugs, autonomic drugs, cardiovascular-renal drugs, endocrine drugs, hematopoietic growth factors, blood lipid lowering drugs, AIDS drugs, modulators of smooth muscle function, antileptics, and psychoactive drugs.

* * * * *

UNITED STATES PATENT AND TRADEMARK OFFICE
CERTIFICATE OF CORRECTION

PATENT NO. : 7,195,780 B2
APPLICATION NO. : 10/274829
DATED : March 27, 2007
INVENTOR(S) : Donn M. Dennis et al.

It is certified that error appears in the above-identified patent and that said Letters Patent is hereby corrected as shown below:

On the Title Page

In column 1, line 1, under "OTHER PUBLICATIONS", after, "polyion" insert --assembly--.

In column 2, line 3, after "Science," delete "(2003)" and substitute --(2000)-- in its place.

In column 2, line 15, before "Replica" delete "Glas" and substitute --Glass-- in its place.

In column 2, line 29, delete "Senior, "Nano-dumping' with" and substitute --Senior, "Nano-dumping" with-- in its place.

In column 2, line 30, after "p. 321" delete "(Aug. 2998)" and substitute --(Aug. 1998)-- in its place.

In column 2, line 5, under "ABSTRACT", after "particular, for the" delete "in vivo" and substitute --*in vivo*-- in its place.

Signed and Sealed this

Third Day of July, 2007

JON W. DUDAS
*Director of the United States Patent and Trademark Office*